United States Patent [19]
Neunhoeffer et al.

[11] Patent Number: 5,663,366
[45] Date of Patent: Sep. 2, 1997

[54] PROCESS FOR THE SYNTHESIS OF 4,5-DIAMINOPYRAZOLE DERIVATIVES USEFUL FOR DYEING HAIR

[75] Inventors: Hans Neunhoeffer, Mühltal; Stefan Gerstung, Reinheim; Thomas Clausen; Wolfgang R. Balzer, both of Alsbach, all of Germany

[73] Assignee: Wella Aktiengesellschat, Darmstadt, Germany

[21] Appl. No.: 650,819

[22] Filed: May 20, 1996

Related U.S. Application Data

[62] Division of Ser. No. 244,553, May 27, 1994.

[30] Foreign Application Priority Data

Oct. 16, 1992 [DE] Germany ............ 42 34 885.4

[51] Int. Cl.$^6$ .................................. C07D 231/38
[52] U.S. Cl. .................... 548/371.4; 548/372.5
[58] Field of Search ................ 548/371.4, 372.5

[56] References Cited

FOREIGN PATENT DOCUMENTS

WO94/08969  4/1994  WIPO .

*Primary Examiner*—Robert W. Ramsuer
*Attorney, Agent, or Firm*—Michael J. Striker

[57] ABSTRACT

The subject matter of the present invention is directed to a process for producing 4,5-diaminopyrazole derivatives of the general formula (I)

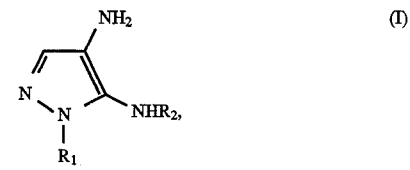

where $R_1$ and $R_2$ independently designate hydrogen, a $C_1$- to $C_6$-alkyl radical or a $C_2$- to $C_4$-hydroxyalkyl radical, which can be used as dye precursors, for example for hair dyes, and to new pyrazole derivatives.

When using the process according to the invention good yields of isomer-pure 4,5-diaminopyrazole derivatives of general formula (I) can be obtained.

2 Claims, No Drawings

PROCESS FOR THE SYNTHESIS OF 4,5-DIAMINOPYRAZOLE DERIVATIVES USEFUL FOR DYEING HAIR

This is a division of application Ser. No. 08/244,553 filed on May 27, 1994 which is a 371 of a PCT/EP93/02644.

The subject matter of the present invention is a process for producing 4,5-diaminopyrazole derivatives of the general formula (I)

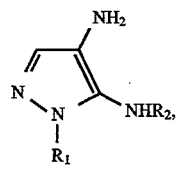

where $R_1$ and $R_2$ independently designate hydrogen, a $C_1$- to $C_6$-alkyl radical or a $C_2$- to $C_4$-hydroxyalkyl radical, and new pyrazole derivatives including 4,5-diaminopyrazole derivatives which can be used as dye precursors, e.g. for hair dyes.

A number of processes for producing 4,5-diaminopyrazole derivatives of formula (I) are already known from the literature on this subject. However, these processes are unsatisfactory in many respects.

For example, according to H. Dorn, et al., *Chem. Ber.* 98, p. 3368 (1965), 5-amino-1-methylpyrazole-4-carboxylic acid is obtained from ethoxymethylene cyanoacetic acid ethyl ester and methylhydrazine and is decarboxylated to obtain 5-amino-1-methylpyrazole in a total yield of 40 percent.

DE-OS 2 141 700 describes a single-step process for obtaining 5-amino-1-methylpyrazole in a yield of 71 percent from N,N-dimethylaminoacrylonitrile and methylhydrazine.

According to M. A. Khan, et al., *Can. J. Chem.* 49, p. 3566 (1971), the 5-amino-1-methylpyrazole obtained, according to the described process, in a yield of 23 percent can be converted to 5-amino-1-methyl-4-nitropyrazole. According to V. P. Perevalov, et al., *Khim. Geterosicl. Soedin.* 8, p. 1090 (1985), catalytic reduction of this product produces 1-methyl-4,5-diaminopyrazole dihydrochloride in a yield of approximately 79 percent. The total yield from the indicated steps is 7 to 13 percent.

Total yields of up to 46 percent are obtained when the 5-amino-1-methylpyrazole is converted with isoamyl nitrite to produce 5-amino-1-methyl-4-nitropyrazole and reduced with zinc(II)chloride to give 4,5-diamino-1-methylpyrazole according to H. Dorn, et al., *Liebigs Ann. Chem.* 717, p. 118 (1968).

A process for producing 4,5-diamino-1-methylpyrazole in which 2-chloroacrylonitrile is cyclized with hydrazine (G. Ege, *Angew. Chem.*, 86, p. 237 (1974)) is known from DE-OS 38 43 892. After acetylation of the amino group, nitration and cleavage of the protective group, the tautomeric compounds 3-amino-4-nitropyrazole and 5-amino-4-nitropyrazole are obtained in a total yield of approximately 41 percent. By alkylating the tautomeric mixture with dimethyl sulfate, an isomeric mixture is obtained in a yield of 70 percent which can be split by chromatography into the isomeric compounds 5'-amino-1-methyl-4-nitropyrazole (25 percent) and 3-amino-1-methyl-4-nitropyrazole (45 percent). The corresponding diamino compounds can be obtained by reduction. The total yield of 1-methyl-4,5-diaminopyrazole is less than 10 percent.

A process for producing 5-amino-1-(2'-hydroxyethyl)-4-nitropyrazole is known from DE-OS 3 432 983. Starting from 5-amino-1-(2'-hydroxyethyl)pyrazole-4-carboxylic acid, the compound is obtained in a yield of 59 percent by decarboxylation, subsequent nitrozation and hydration.

Aside from their small yields in some cases, the described processes exhibit other disadvantages. For example, many starting compounds such as ethoxymethyl cyanoacetic acid ethyl ester and N,N-dimethylaminoacrylonitrile are not available commercially or can only be produced by synthesis at high cost in some cases. Moreover, hydrazine derivatives are classified as poisonous and in some cases carcinogenic.

The production of 4,5-diaminopyrazole derivatives which are substituted in the nitrogen atom of the amino group in the 5-position is not described.

The object of the present invention was therefore to provide a process for pure isomeric production of differently substituted 4,5-diaminopyrazole derivatives.

It has now been found that this object is met in an outstanding manner by a process for the production of 4,5-diaminopyrazole derivatives of the general formula (I)

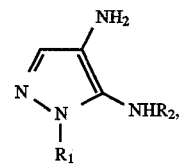

where $R_1$ and $R_2$ independently designate hydrogen, a $C_1$- to $C_6$-alkyl radical or a $C_2$- to $C_4$-hydroxyalkyl radical, characterized in that (A) 3,5-dibromo-4-nitropyrazole is converted with a $C_1$- to $C_6$-alkyl halide, a $C_2$- to $C_4$-hydroxyalkyl halide or benzyl halide or a $C_1$- to $C_6$-alkyl, $C_2$- to $C_4$-hydroxyalkyl sulfate or benzyl sulfate to form compounds of the form compounds of the general formula (II)

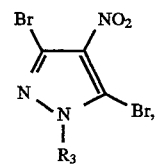

where $R_3$ is a $C_1$- to $C_6$-alkyl radical, a $C_2$- to $C_4$-hydroxyalkyl radical or a benzyl radical, (B) the compounds of general formula (II) are substituted in the 5-position with $C_1$- to $C_6$-alkyl amine, $C_2$- to $C_4$-hydroxyalkyl amine or benzyl amine to form compounds of the general formula (III)

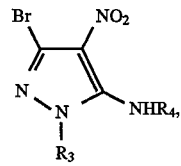

where $R_3$ and $R_4$ independently designate a $C_1$- to $C_6$-alkyl radical, a $C_2$- to $C_4$-hydroxyalkyl radical or a benzyl radical, and (C) the compounds of general formula (III) are reduced by catalytic hydrogenation to form compounds of general formula (I).

The process described above is therefore included in the subject matter of the invention.

The general reaction diagram is illustrated below.

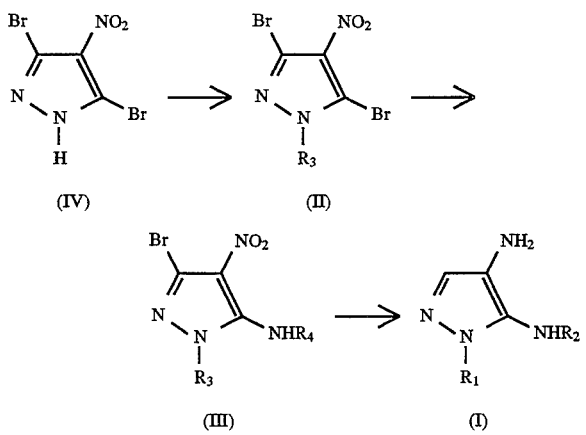

The known 3,5-dibromo-4-nitropyrazole (IV) serves as starting compound for the synthesis of 4,5-diaminopyrazole derivatives (I) and can be produced as follows:

According to R. Hüttel, et al., Chem. Ber. 88, p. 1577 (1955), nitration of pyrazole with a mixture of sulfuric acid and nitric acid produces the 4-nitropyrazole which, according to H. J. Klebe, et al., Synthesis 1973, p. 294, can be obtained under gentler conditions by nitration of pyrazole to form N-nitropyrazole and subsequent transposition by sulfuric acid (R. Hüttel, et al., Chem. Ber. 88, p. 1577 (1955). Subsequent bromation according to J. P. H. Juffermanns, et al., J. Org. Chem. 51, p. 4656 (1986) gives 3,5-dibromo-4-nitropyrazole (IV).

In the process according to the invention, the 3,5-dibromo-4-nitropyrazole (IV) is first alkylated in the 1-position by converting with $C_1$- to $C_6$-alkyl halides, $C_2$- to $C_4$-hydroxyalkyl halides or benzyl halides in dimethylformamide (DMF) (method I) or by converting with $C_1$- to $C_6$-alkyl sulfate, $C_2$- to $C_4$-hydroxyalkyl sulfate or benzyl sulfate and caustic solution (method II).

In method I, 3,5-dibromo-4-nitropyrazole dissolved in absolute DMF is added in an equimolar amount dropwise to sodium hydride in absolute DMF over a period of one hour with stirring at room temperature. Following cessation of gas generation, an equimolar amount of $C_1$- to $C_6$-alkyl halide, $C_2$- to $C_4$-hydroxyalkyl halide or benzyl halide, preferably benzyl chloride or benzyl bromide, dissolved in DMF is added dropwise and the reaction mixture is heated for three hours at 80° C. The solvent is then vacuum distilled and the residue is recrystallized from methylene chloride.

According to method II, the 3,5-dibromo-4-nitropyrazole is dissolved in an aqueous caustic solution, preferably 2N caustic sodium or potassium hydroxide solution and mixed with two to five times the molar amount of $C_1$- to $C_6$-alkyl sulfate, $C_2$- to $C_4$-hydroxyalkyl sulfate or benzyl sulfate. The reaction is allowed to run during 15 hours at room temperature accompanied by vigorous stirring, the precipitated product is filtered and washed with water until the washing solution reacts with neutral pH and is vacuum dried.

Both processes produce good yields of pure isomeric N-substituted 3,5-dibromo-4-nitropyrazoles of general formula (II).

In a subsequent step, the N-substituted 3,5-dibromo-4-nitropyrazoles of general formula (II) are heated in an aqueous, alcoholic or aqueous-alcoholic solution of $C_1$- to $C_6$-alkyl amine, $C_2$- to $C_4$-hydroxyalkyl amine or benzyl amine or in the corresponding amine itself, as solvent, at a temperature of 60° to 80° C. Methanol and/or ethanol are preferably used as alcohols. After a reaction period of 1 to 20 hours, the cooled reaction mixture is poured on 20 to 150 ml water and the separated product is filtered out, washed with water (10 to 20 ml) and vacuum dried. Good yields of pure isomeric 5-amino-3-bromo-4-nitropyrazole derivatives of general formula (III) are obtained.

The compounds of general formula (III) are then hydrogenated using a palladium-on-activated-carbon catalyst with a palladium content of 10 percent by weight. For this purpose, the present invention provides two methods. According to method (1), a small amount of the catalyst, approximately 100 mg, are added to the alcoholic solution, preferably ethanol, of a compound of general formula (III) and the preparation is transferred to an autoclave. At 50 bar hydrogen atmosphere, the preparation is stirred at room temperature for 1 to 6 hours, preferably 2 to 4 hours. The catalyst is then filtered over a glass filter crucible and the product is precipitated as salt with sulfuric acid in an equimolar amount with respect to the pyrazole compound or twice the molar amount of hydrochloric acid. According to method (2), a small amount of the above-described catalyst and an equimolar amount of sulfuric acid with respect to the starting compound are added to the aqueous solution of a compound of general formula (III) and the preparation is shaken in a hydrogenation flask at room temperature in a hydrogen atmosphere (normal pressure). When thin-layer chromatographic analysis of the reaction mixture shows no further evidence of educt, the reaction mixture is filtered over a glass filter crucible and the filtrate is reduced and the product crystallized from ethanol.

Good yields of isomer-pure 4,5-diaminopyrazole derivatives of general formula (I) are obtained by both methods.

The compounds of general formula (I) in which $R_1$ is hydrogen are present as tautomers. The 3- and 5-positions in the pyrazole ring are not distinguishable.

When reducing compounds of general formula (III) in which $R_3$ is a benzyl radical or $R_4$ is a benzyl radical or a tert-butyl radical, the N-benzyl radicals and N-tert-butyl radicals are split by reduction so as to obtain compounds of general formula (I) in which $R_1$ or $R_2$ are hydrogen instead of benzyl or tert-butyl.

The subject matter of the present patent application also includes 3,5-dibromo-4-nitropyrazole derivatives of general formula (II)

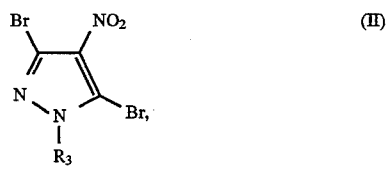

where $R_3$ is a $C_1$- to $C_6$-alkyl radical, a $C_2$- to $C_4$-hydroxyalkyl radical or a benzyl radical. Examples for compounds of formula (II) are 3,5-dibromo-1-methyl-4-nitropyrazole, 3,5-dibromo-1-ethyl-4-nitropyrazole, 3,5-dibromo-1-isopropyl-4-nitropyrazole, 3,5-dibromo-1-(2'-hydroxyethyl)-4-nitropyrazole and 1-benzyl-3,5-dibromo-4-nitropyrazole.

The subject matter of the invention also includes 3-bromo-5-amino-4-nitropyrazole derivatives of general formula (III)

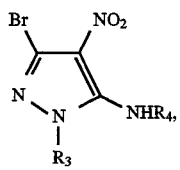

(III)

where R₃ and R₄ independently designate a $C_1$- to $C_6$-alkyl radical, $C_2$- to $C_4$-hydroxyalkyl radical or a benzyl radical.

Examples for compounds of formula (III) are
3-bromo-1-methyl-5-methylamino-4-nitropyrazole,
3-bromo-5-(2'-hydroxyethyl)amino-1-methyl-4-nitropyrazole,
3-bromo-5-tert-butylamino-1-methyl-4-nitropyrazole,
5-benzylamino-3-bromo-1-methyl-4-nitropyrazole,
5-benzylamino-3-bromo-1-ethyl-4-nitropyrazole,
5-benzylamino-3-bromo-1-isopropyl-4-nitropyrazole,
3-bromo-1-(2'-hydroxyethyl)-5-(2'-hydroxyethyl)amino-4-nitropyrazole,
3-bromo-1-(2'-hydroxyethyl)-5-methylamino-4-nitropyrazole,
5-benzylamino-3-bromo-1-(2'-hydroxyethyl)-4-nitropyrazole,
1-benzyl-3-bromo-5-methylamino-4-nitropyrazole,
1-benzyl-3-bromo-5-ethylamino-4-nitropyrazole,
1-benzyl-3-bromo-5-(2'-hydroxyethyl)amino-4-nitropyrazole and
1-benzyl-5-benzylamino-3-bromo-4-nitropyrazole.

The subject matter of the present invention further includes new 4,5-diaminopyrazole derivatives of the general formula (V)

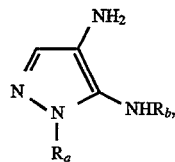

(V)

where $R_a$ and $R_b$ are hydrogen, a $C_1$- to $C_6$-alkyl radical or a $C_2$- to $C_4$-hydroxyalkyl radical, provided that $R_a$ is not hydrogen, methyl or 2-hydroxyethyl when $R_b$ is hydrogen.

Examples of compounds of formula (I) are
4-amino-1-methyl-5-methylaminopyrazole,
4-amino-5-(2'-hydroxyethyl)amino-1-methylpyrazole,
4,5-diamino-1-ethylpyrazole,
4,5-diamino-1-isopropylpyrazole,
4-amino-1-(2'-hydroxyethyl)-5-(2'-hydroxyethyl)aminopyrazole,
4-amino-1-(2'-hydroxyethyl)-5-methylaminopyrazole,
4-amino-(3)5-methylaminopyrazole,
4-amino-(3)5-ethylaminopyrazole and
4-amino-(3)5-(2'-hydroxyethyl)aminopyrazole.

The compounds of formula (V) can be used as dye precursors in oxidative hair dye compositions for dyeing hair (see Application Example).

EXAMPLES

Production of N-substituted 3,5-dibromo-4-nitropyrazoles of general formula (II)

a) General directions, method I:

19.0 g (70 mmoles) 3,5-dibromo-4-nitropyrazole dissolved in 90 ml absolute DMF are added dropwise to 1.75 g (70 mmoles) sodium hydride in 150 ml absolute DMF (dimethylformamide) over a period of 1 hour. After cessation of gas generation, 70 mmoles $C_1$- to $C_6$-alkyl halide, $C_2$- to $C_4$-hydroxyalkyl halide or benzyl halide are added dropwise to 30 ml DMF and heated at 80° C. for 3 hours. The solvent is then vacuum distilled and the residue is recrystallized from methylene chloride.

b) General directions, method II:

92.5 mmoles $C_1$- to $C_6$-alkyl sulfate, $C_2$- to $C_4$-hydroxyalkyl sulfate or benzyl sulfate are added to a solution of 5 g (18.5 mmoles) 3,5-dibromo-4-nitropyrazole in 50 ml 2N sodium hydroxide solution, vigorously stirred for 15 hours at room temperature and finally the precipitated product is filtered out, washed with water until the washing solution reacts at neutral pH, and vacuum dried.

Production example 1

3,5-dibromo-1-methyl-4-nitropyrazole

In method II using methyl sulfate, 5.06 g (96 percent of theory) of 3,5-dibromo-1-methyl-4-nitropyrazole are obtained in the form of white crystals with a melting point of 154° C.

$^1$H-NMR (60 MHz, DMSO-$d_6$):=3.90 ppm (s; 3H; —CH₃).

In this and in all of the following $^1$H-NMR spectra: chemical shift is indicated in delta (ppm), the coupling constants (J) are indicated in Hertz.

Standard: tetramethylsilane
s=singlet, d=doublet, t=triplet, q=quartet, m=multiplet,
Ph=phenyl, ring-H=proton on pyrazole ring
MS (70 eV): m/e=287 (M⁺).

Production example 2

3,5-dibromo-1-ethyl-4-nitropyrazole

In method II using ethyl sulfate, 3.59 g (65 percent of theory) of 3,5-dibromo-1-ethyl-4-nitropyrazole are obtained in the form of white crystals with a melting point of 119° to 121° C.

$^1$H-NMR (60 MHz, DMSO-$d_6$):=4.26 (q; J=7.0 Hz; 2H; —CH₂—CH₃) and 1.36 ppm (t; J=7.0 Hz; 3H; —CH₂—CH₃).

MS (70 eV): m/e=297 (M⁺).

Production example 3

3,5-dibromo-1-isopropyl-4-nitropyrazole

In method I using 2-bromopropane, 13.14 g (60 percent of theory) of 3,5-dibromo-1-isopropyl-4-nitropyrazole are obtained in the form of brownish yellow crystals with a melting point of 72° to 73° C.

$^1$H-NMR (60 MHz, DMSO-$d_6$):=4.84 (dq; J=6.5 Hz; 1H; —CH) and 1.42 ppm (d; J=6 Hz; 6H; —CH(CH₃)₂.

MS (70 eV): m/e=311 (M⁺).

Production example 4

3,5-dibromo-1-(2'-hydroxyethyl)-4-nitropyrazole

In method I using 1-bromo-2-hydroxyethane, 14.77 g (67 percent of theory) of 3,5-dibromo-1-(2'-hydroxyethyl)-4-nitropyrazole are obtained in the form of pale yellow crystals with a melting point of 103° to 105° C.

$^1$H-NMR (60 MHz, DMSO-$d_6$):=4.90 (s; wide; 1H; —OH; exchangeable with D₂O), 4.31 (m; 2H; —CH₂—) and 4.08–3.82 ppm (m; 2H; —CH₂—; after D₂O exchange: t; 2H; J=5 Hz).

MS (70 eV): m/e=317 (M⁺)

Production example 5

1-benzyl-3,5-dibromo-4-nitropyrazole

In method I using benzyl chloride, 17.94 g (71 percent of theory) of 1-benzyl-3,5-dibromo-4-nitropyrazole are obtained in the form of pale yellow crystals with a melting point of 128° C.

$^1$H-NMR (60 MHz, DMSO-$d_6$):=7.26–7.41 (m; 5H; Ph-H) and 5.51 ppm (s; 2H; —$CH_2$—).

MS (70 eV): m/e=363 ($M^+$).

B) Production of 5-amino-3-bromo-4-nitropyrazole derivatives of general formula (III)

Production example 6

3-bromo-1-methyl-5-methylamino-4-nitropyrazole 2 g (7.02 mmoles) of 3,5-dibromo-1-methyl-4-nitropyrazole are heated in 50 ml of a 40-percent solution of methylamine in ethanol for 4 hours at boiling temperature. After cooling, 100 ml water are added to the reaction mixture, the separated product is filtered out and washed with a small amount of water (20 ml). After vacuum drying, 1.45 g (88 percent of theory) of 3-bromo-1-methyl-5-methylamino-4-nitropyrazole are obtained in the form of yellow crystals with a melting point of 185° C.

$^1$H-NMR (60 MHz, DMSO-$d_6$):=7.50 (s; wide; 1H; —NH; exchangeable with $D_2O$), 3.88 (s; 3H; N—$CH_3$) and 3.16 ppm (d; 3H; J=6 Hz; —NH—$\underline{CH_3}$; s after exchanging with $D_2O$).

MS (70 eV):m/e=236 ($M^+$).

Production example 7

3-bromo-5-(2'-hydroxyethylamino)-1-methyl-4-nitropyrazole 3 g (10.5 mmoles) of 3,5-dibromo-1-methyl-4-nitropyrazole are heated in a solution of 30 ml ethanolamine in 30 ml ethanol for 15 hours at boiling temperature. The reaction mixture is then poured on 200 ml water, the separated product is filtered, washed with water (20 ml) and vacuum dried. Additional product crystallizes from the filtrate when cooled (5° C.). 2.25 g (81 percent of theory) of 3-bromo-5-(2'-hydroxyethyl)amino-1-methyl-4-nitropyrazole are obtained in the form of yellow crystals with a melting point of 150° C.

$^1$H-NMR (60 MHz, DMSO-$d_6$): =7.38 (s; wide; 1H; —NH; exchangeable with $D_2O$), 4.98 (s; wide; 1H; —OH; exchangeable with $D_2O$), 3.82 (s; 3H; N—$CH_3$) and 3.60 ppm (m; 4H; —NH —$\underline{CH_2}$—$\underline{CH_2}$).

MS (70 eV):m/e=266 ($M^+$).

Production example 8

3-bromo-5-tert-butylamino-1-methyl-4-nitropyrazole 1.5 g (5.26 mmoles) of 3,5-dibromo-1-methyl-4-nitropyrazole are heated in a solution of 20 ml tert-butylamine in 30 ml ethanol for 20 hours at boiling temperature. After cooling, the reaction mixture is poured on 150 ml water, the separated product is filtered and washed with 100 ml water. After vacuum drying, 1.14 g (78 percent of theory) of 3-bromo-5-tert-butylamino-1-methyl-4-nitropyrazole are obtained in the form of pale yellow flakes with a melting point of 75° to 77° C.

$^1$H-NMR (60 MHz, DMSO-$d_6$):=5.35 (s; 1H; —NH; exchanges with $D_2O$), 3.75 (s; 3H; N—$CH_3$) and 1.20 ppm (s; 9H; —$C(CH_3)_3$).

MS (70 eV): m/e=277 ($M^+$).

Production example 9

5-benzylamino-3-bromo-1-methyl-4-nitropyrazole 2 g (7.02 mmoles) of 3,5-dibromo-1-methyl-4-nitropyrazole are heated in a solution of 11 g (0.1 mole) of benzylamine in 50 ml ethanol for 10 hours at boiling temperature. After cooling, the reaction mixture is poured on 100 ml water, the separated product is filtered and washed with water (20 ml). After vacuum drying, 1.76 g (81 percent of theory) of 5-benzylamino-3-bromo-1-methyl-4-nitropyrazole are obtained in the form of yellow needles with a melting point of 133° C.

$^1$H-NMR (60 MHz, DMSO-$d_6$):=7.88 (t; 1H; J=6 Hz; —NH; exchangeable with $D_2O$), 7.32 (m; 5H; Ph-H), 4.73 (d; 2H; J=6 Hz; —NH—$\underline{CH_2}$—; s after exchanging with $D_2O$) and 3.68 ppm (s; 3H; N—$CH_3$).

MS (70 eV): m/e=312 ($M^+$).

Production example 10

5-benzylamino-3-bromo-1-ethyl-4-nitropyrazole 6.3 g (21 mmoles) of 3,5-dibromo-1-ethyl-4-nitropyrazole are heated in 10 ml benzylamine for 1 hour at 80° C. The reaction mixture is then poured on 50 ml water and the separated oil is collected. The product is crystallized from the oil by adding 20 to 30 ml acetic acid ethyl ester. After recrystallizing from methanol once, 5.2 g (76 percent of theory) of 5-benzylamino-3-bromo-1-ethyl-4-nitropyrazole are obtained n the form of bright yellow needles with a melting point of 92° C.

$^1$H-NMR (300 MHz, DMSO-$d_6$):=7.90 (t; J=6.7 Hz; 1H; —NH; exchanges with $D_2O$), 7.26–7.40 (m; 5H; Ph-H), 4.68 (d; J=6.7 Hz, 2H; NH—$\underline{CH_2}$—; s after exchange with $D_2O$), 4.00 (q; J=7.3 Hz; 2H; —$\underline{CH_2}$—$CH_3$), and 1.18 ppm (t; J=7.2 Hz; 3H; —$CH_2$—$\underline{CH_3}$).

MS (70 eV): m/e=324 ($M^+$).

Production example 11

5-benzylamino-3-bromo-1-isopropyl-4-nitropyrazole 3.13 g (10 mmoles) of 3,5-dibromo-1-isopropyl-4-nitropyrazole are heated in 10 ml benzylamine for 1 hour at 80° C. The reaction mixture is then poured on 50 ml water and the separated product is filtered. After recrystallization once from a toluene/petroleum ether mixture (1:1), 2.3 g (68 percent of theory) of 5-benzylamino-3-bromo-1-isopropyl-4-nitropyrazole are obtained in the form of bright yellow crystals with a melting point of 120 and 122° C.

$^1$H-NMR (300 MHz, DMSO-$d_6$):=7.78 (t; J=6.6 Hz; 1H; —NH; s after exchange with $D_2O$), 7.25–7.39 (m; 5H; Ph-H); 4.66 (d; J=6.6 Hz, 2H; NH—$\underline{CH_2}$—; s after exchange with D2O), 4.57 (dq; J=6.4 Hz; 1H; —$\underline{CH}(CH_3)_2$, and 1.19 ppm (d; J=6.4 Hz; 6H; —$CH(\underline{CH_3})_2$).

MS (70 eV): m/e 338 ($M^+$).

Production example 12

3-bromo-1-(2'-hydroxyethyl)-5-(2'-hydroxyethyl)amino-4-nitropyrazole 1.5 g (4.8 mmoles) of 3,5-dibromo-1-(2'-hydroxyethyl)-4-nitropyrazole are heated in a solution of 0.58 g (9.6 mmoles) ethanolamine in 30 ml ethanol for 15 hours at 80° C. After cooling, 50 ml of water are added to the reaction mixture which is then extracted three times with 70 ml of acetic acid ethyl ester. 200 ml n-hexane are added to the purified extraction solutions and the solvent mixture is vacuum distilled to a third of its original amount. Once again, n-hexane is added until the solution becomes cloudy. The crystallized product is then collected by filtration and washed with n-hexane (10 to 20 ml). 1.04 g (74 percent of theory) of 3-bromo-1-(2'-hydroxyethyl)-5-(2'-hydroxyethyl)amino-4-nitropyrazole are obtained in the form of bright yellow crystals with a melting point of 132° to 134° C.

$^1$H-NMR (60 MHz, DMSO-d$_6$):=7.42 (s; wide; 1H; —NH; exchangeable with D$_2$O), 5.23–5.02 (m; 2H; —OH; exchangeable with D$_2$O), 4.18 (m; 2H; N—CH$_2$—), 3.93–3.45 ppm (m; 6H; —CH$_2$—).

MS (70 eV): m/e=296 (M$^+$).

Production example 13

3-bromo-1-(2'-hydroxyethyl)-5-methylamino-4-nitropyrazole 3.15 g (10 mmoles) of 3,5-dibromo-1-(2'-hydroxyethyl)-4-nitropyrazole are heated in 70 ml of a 30-percent solution of methylamine in water for 1 hour at 60° C. After cooling, the product precipitates in the form of bright yellow crystals with a melting point of 158° to 160° C. 2.4 g (91 percent of theory) of 3-bromo-1-(2'hydroxyethyl)-5-methylamino-4-nitropyrazole are obtained.

$^1$H-NMR (300 MHz, DMSO-d$_6$):=7.67 (s; 1H; —NH; exchanges with D$_2$O), 5.06 (s; 1H; —OH; exchanges with D$_2$O), 4.18 (t; 2H; N—CH$_2$—), 3.68 (t; 2H; —C$\underline{H}_2$—OH) and 3.15 ppm (d; J=4.5 Hz; 3H; —NH—C$\underline{H}_3$; s after D$_2$O exchange).

MS (70 eV): m/e=266 (M$^+$).

Production example 14

5-benzylamino-3-bromo-1-(2'-hydroxyethyl)-4-nitropyrazole 6.3 g (20 mmoles) 3,5-dibromo-1-(2'-hydroxyethyl)-4-nitropyrazole are heated in 20 ml benzylamine for 2 hours at 60° C. After cooling, the reaction mixture is poured on 50 ml of water, the separated product is filtered and recrystallized once from toluene/ligroine (1:1). 4 g (59 percent of theory) of 5-benzylamino-3-bromo-1-(2'-hydroxyethyl)-4-nitropyrazole are obtained in the form of yellow crystals with a melting point of 133° to 135° C.

$^1$H-NMR (300 MHz, DMSO-d$_6$):=7.89 (t; J=6.6 Hz; 1H; —NH; exchanges with D$_2$O), 7.22–7.44 (m; 5H; Ph-H); 5.15 (s; 1H; —OH; exchanges with D$_2$O), 4.77 (d; J=6.6 Hz; 2H; —NH—C$\underline{H}_2$—); s after exchange with D$_2$O), 3.99 (t; J=4.9 Hz; 2H; —C$\underline{H}_2$—) and 3.96 ppm (t; J=5 Hz; 2H; —CH$_2$—).

MS (70 eV): m/e=340 (M$^+$).

Production example 15

1-benzyl-3-bromo-5-methylamino-4-nitropyrazole 3.61 g (10 mmoles) of 1-benzyl -3,5-dibromo-4-nitropyrazole are heated in 100 ml of a 35-percent solution of methylamine in water for 4 hours at 60° C. After cooling, the separated precipitate is collected by filtration and recrystallized once from ethanol. 2.7 g (87 percent of theory) of 1-benzyl-3-bromo-5-methylamino-4-nitropyrazole are obtained in the form of colorless crystals with a melting point of 116° C.

$^1$H-NMR (300 MHz, DMSO-d$_6$):=7.71 (s; 1H; —NH; exchanges with D$_2$O), 7.15–7.40 (m; 5H; Ph-H), 5.45 (s; 2H; —CH$_2$—) and 3.02 ppm (s; 3H; —CH$_3$).

MS (70 eV): m/e=312 (M$^+$).

Production example 16

1-benzyl-3-bromo-5-ethylamino-4-nitropyrazole 3.61 (10 mmoles) of 1-benzyl-3,5-dibromo-4-nitropyrazole are heated at 60° C. in 120 ml of a 30-percent aqueous ethylamine solution for 1 hour. After cooling, the product separates in the form of colorless crystals with a melting point of 122° C. 2.88 g (89 percent of theory) of 1-benzyl-3-bromo-5-ethylamino-4-nitropyrazole are obtained.

$^1$H-NMR (300 MHz, DMSO-d$_6$):=7.15–7.41 (m; 6H; —NH and Ph-H; 1H exchanges with D$_2$O), 5.37 (s; 1H; —CH$_2$—), 3.32–3.39 (m; 2H; —C$\underline{H}_2$—CH$_3$) and 1.07–1.12 ppm (t; 3H; —CH$_2$—C$\underline{H}_3$).

MS (70 eV): m/e=326 (M$^+$).

Production example 17

1-benzyl-3-bromo-5-(2'-hydroxyethyl)amino-4-nitropyrazole 3.61 (10 mmoles) of 1-benzyl-3,5-dibromo-4-nitropyrazole are heated at 80° C. in 15 ml ethanolamine for 2 hours. After cooling, the reaction mixture is poured on 30 ml water and the separated precipitate is collected by filtration. After recrystallizing once from toluene, 2.5 g (74 percent of theory) of 1-benzyl-3-bromo-5-(2'-hydroxyethyl)amino-4-nitropyrazole are obtained in the form of pale yellow crystals with a melting point of 110° to 112° C.

$^1$H-NMR (300 MHz, DMSO-d$_6$):=7.54 (t; 1H; —NH; exchanges with D$_2$O), 7.15–7.40 (m; 5H; Ph-H), 5.44 (s; 2H; —C$\underline{H}_2$—Ph), 5.05 (t; 1H; —OH; exchanges with D$_2$O) and 3.32–3.53 ppm (m; 4H; —C$\underline{H}_2$—C$\underline{H}_2$).

MS (70 eV): m/e=342 (M$^+$).

Production example 18

1-benzyl-5-benzylamino-3-bromo-4-nitropyrazole 3.61 (10 moles) of 1-benzyl-3,5-dibromo-4-nitropyrazole are heated at 60° C. in a solution of 3.6 g benzylamine for 2 hours. After cooling, the reaction mixture is poured on 20 ml of water and the separated precipitate is filtered out. After recrystallizing once from a mixture of ligroine and toluene (1:1), 2.6 g (68 percent of theory) of 1-benzyl-5-benzylamino-3-bromo-4-nitropyrazole are obtained in the form of pale yellow crystals with a melting point of 103° C.

$^1$H-NMR (300 MHz, DMSO-d$_6$):=8.04 (t; J=6.1 Hz; 1H; —NH; exchanges with D$_2$O), 7.08–7.47 (m; 1OH; Ph-H), 5.24 (s; 2H; —C$\underline{H}_2$—Ph), and 4.55 ppm (d; J=6.1 Hz; 2H; —NH—C$\underline{H}_2$—Ph; s after D$_2$O exchange).

MS (70 ev): m/e=388 (M$^+$).

C) Production of 4,5-diaminopyrazole derivatives of general formula (I)

a) General directions, method (1):

A compound of general formula (II) in the amount indicated in the following production examples is dissolved in 130 ml ethanol and transferred to an autoclave (250 ml). After adding a small amount (approximately 100 mg) of palladium-on-activated-carbon catalyst with a palladium content of 10% by weight, the mixture is stirred at 50 bar hydrogen atmosphere at room temperature for the period of time indicated in the following production examples. The reaction mixture is then transferred to a glass flask via a glass filter pump and the catalyst is immediately filtered out over a glass filter crucible. Sulfuric acid (97-percent) in an equimolar amount with respect to the starting compound or twice the molar amount of hydrochloric acid (36-percent) is then added to the filtrate.

b) General directions, method (2):

A compound of general formula (III) in the amount indicated in the following production 'examples is shaken in a hydrogenating flask with an equimolar amount of 97-percent sulfuric acid, a small amount (2 spatula tips) of palladium-on-activated-carbon catalyst (palladium content 10% by weight) and water in the indicated amount at room temperature in a hydrogen atmosphere (normal pressure) over the period of time indicated in the following production examples. The course of the reaction is monitored by thin layer chromatography. After complete conversion of the educt, the reaction mixture is filtered over a glass filter crucible. After distilling the solvent, the product is crystallized from ethanol.

Production example 19

4-amino-1-methyl-5-methylaminopyrazole 0.5 g (2.13 mmoles) of 3-bromo-1-methyl-5-methylamino-4-nitropyrazole are hydrogenated in a solution of 220 mg (2.13 mmoles) sulfuric acid in 20 ml water for 14 hours after adding the catalyst as described in method (2). After filtering the catalyst, the filtrate is reduced until dry and the residue is recrystallized from ethanol. 370 mg (78 percent of theory) of 4-amino-1-methyl-5-methylaminopyrazole hydrosulfate are obtained in the form of colorless crystals with a melting point of 185° to 188° C.

$^1$H-NMR (60 MHz, DMSO-$d_6$):=8.53 (s; wide; 5H, —NH$_2$; —NH; H$_2$SO$_4$; exchangeable with D$_2$O), 7.30 (s; 1H; ring-H 3.58 (s; 3H; N—CH$_3$) and 2.80 ppm (s; 3H; —NH—$\underline{CH_3}$).

MS (70 eV): m/e=126 (M$^+$).

Production example 20

4-amino-5-(2'-hydroxyethyl)amino-1-methylpyrazole 1 g (3.77 mmoles) of 3-bromo-5-(2'-hydroxyethyl)amino-1-methyl-4-nitropyrazole are hydrogenated in a solution of 380 mg (3.77 mmoles) sulfuric acid in 50 ml water for 2 hours according to method (2). 720 mg (75 percent of theory) of 4-amino-5-(2'-hydroxyethyl)amino-1-methylpyrazole hydrosulfate are obtained in the form of colorless crystals with a melting point of 94° to 97° C.

$^1$H-NMR (60 MHz, DMSO-$d_6$):=8.00 (s; wide; 6H, —NH$_2$; —NH, —OH; H$_2$SO$_4$; exchanges with D$_2$O), 7.45 (s; 1H; ring-H), 3.60 (s; 3H; —CH$_3$) and 3.50–310 ppm (s; 4H; —$\underline{CH_2}$—$\underline{CH_2}$).

MS (70 eV): m/e=156 (M$^+$).

Production example 21

4,5-diamino-1-methylpyrazole a) 0.5 g (1.81 mmoles) of 3-bromo-5-tert-butylamino-1-methyl-4-nitropyrazole are hydrogenated for 48 hours according to method (2) in a solution of 1.84 mg (1.81 mmoles) sulfuric acid in 20 ml water after addition of the catalyst. After distilling the solvent to half the original amount and adding an equal amount of ethanol, 360 mg (87 percent of theory) of 4, 5-diamino-1-methylpyrazole hydrosulfate hydrate are obtained in the form of white crystals with a melting point of 200° to 201° C.

b) 0.5 g (1.61 mmoles) of 5-benzylamino -3-bromo-1-methyl-4-nitropyrazole are hydrogenated for 48 hours as described in method (2) in a solution of 165 mg (161 mmoles) sulfuric acid in 20 ml water after adding the catalyst. The catalyst is then filtered and the filtrate is reduced to approximately 2 ml. After adding a little ethanol (approximately 2 ml), the product separates in the form of white crystals. 330 mg (90 percent of theory) of 4,5-diamino-1-methylpyrazole hydrosulfate hydrate are obtained in the form of white crystals with a melting point of 200° to 201° C.

Production example 22

4,5-diamino-1-ethylpyrazole 1.62 g (5.6 mmoles) of 5-benzylamino-3-bromo-1-ethyl-4-nitropyrazole are hydrogenated over a period of 2 hours according to method (1). After filtering the catalyst and adding 1 ml (11.6 mmoles) concentrated hydrochloric acid (36-percent), the product precipitates as dihydrochloride. 0.8 g (72 percent of theory) of4,5-diamino-1-ethylpyrazole dihydrochloride are obtained in the form of colorless crystals with a melting point of 184° to 186° C.

$^1$H-NMR (300 MHz, DMSO-$d_6$):=8.01 (s; wide; 6H, —NH$_2$; HCl; exchanges with D$_2$O), 7.63 (s; 1H; ring-H; 4.03 (q; J=6.4 Hz; 2H; —$\underline{CH_2}$—CH$_3$) and 1.25 ppm (t; J=6.5 Hz; 3H; —CH$_2$—$\underline{CH_3}$).

MS (70 eV): m/e=126 (M$^+$).

Production example 23

4,5-diamino-1-isopropylpyrazole 0.5 g (1.6 mmoles) of 5-benzylamino-3-bromo-1-isopropyl-4-nitropyrazole are hydrogenated for 2 hours according to method (1). After filtering the catalyst and adding 0.3 ml (3.5 mmoles) concentrated hydrochloric acid, the product precipitates as dihydrochloride. 0.25 g (73 percent of theory) of4,5-diamino-1-isopropylpyrazole dihydrochloride is obtained in the form of colorless crystals with a melting point of 164° C.

$^1$H-NMR (300 MHz, DMSO-$d_6$):=7.90 (s; wide; 6H, —NH$_2$; HCl ; exchanges with D$_2$O), 7.51 (s; 1H; ring-H), 4.54 (m; 1H; —$\underline{CH}$(CH$_3$)$_2$) and 1.30 ppm (d; 6H—CH($\underline{CH_3}$)$_2$).

MS (70 eV): m/e=140 (M$^+$).

Production example 24

4-amino-1-(2'-hydroxyethyl)-5-(2'-hydroxyethyl) amino-pyrazole 0.8 g (2.7 mmoles) of 3-bromo-1-(2'-hydroxyethyl)-5-(2'-hydroxyethyl)amino-4-nitropyrazole are hydrogenated over a period of 4 hours according to method (1). After filtering the catalyst, 0.27 g (2.7 mmoles) sulfuric acid (97-percent) is added. After cooling to −30° C., 630 mg (82 percent of theory) of 4-amino-1-(2'-hydroxyethyl)-5-(2'-hydroxyethyl) aminopyrazole hydrosulfate are obtained in the form of colorless crystals with a melting point of 140° to 142° C.

$^1$H-NMR (60 MHz, DMSO-$d_6$):=10.18 (s; wide; 7H, —NH; —NH$_2$; —OH; H$_2$SO$_4$; exchangeable with D$_2$O), 7.37 (s; 1H; ring-H), 4.00 (m; 2H; —CH$_2$—), 3.53 (m; wide; 4H; —CH$_2$—) and 3.13 ppm (m; 2H; —CH$_2$—).

MS (70 eV): m/e=186 (M$^+$).

Production example 25

4-amino-1-(2'-hydroxyethyl)-5-methylaminopyrazole 2.65 g (10 mmoles) of 3-bromo-1-(2'-hydroxyethyl)-5-methylamino-4-nitropyrazole are hydrogenated for 4 hours according to method (1). After adding 1 g (10 mmoles) sulfuric acid and 10 ml isopropanol, the product separates. 1 g (40 percent of theory) of 4-amino-1-(2'-hydroxyethyl)-5-methylaminopyrazole hydrosulfate are obtained in the form of colorless crystals with a melting point of 138° to 140° C.

$^1$H-NMR (300 MHz, DMSO-d$_6$):=9.6 (s; 2H, —NH$_2$, exchanges with D$_2$O), 7.38 (s; 1H; ring-H), 6.35 (s; 2H; —NH and —OH; exchanges with D$_2$O), 3.96 '(t; J=5.8 Hz; 2H; —CH$_2$—CH$_2$), 3.65 (t; J=5.7 Hz; 2H; —CH$_2$—CH$_2$—) and 2.80 ppm (s; 3H; —NH—CH$_3$).

MS (70 eV): m/e=156 (M$^+$).

Production example 26

4,5-diamino-1-(2'-hydroxyethyl)pyrazole 1.7 g (5 mmoles) of 5-benzylamino-3-bromo-1-(2'-hydroxyethyl)-4-nitropyrazole are hydrogenated for 4 hours according to method (1). After adding 0.5 g (5 mmoles) of sulfuric acid, 0.8 g (62 percent of theory) of 4,5-diamino-1-(2'-hydroxyethyl)pyrazole hydrosulfate hydrate are obtained in the form of colorless crystals with a melting point of 158° to 160° C.

Production example 27

4-amino-(3)5-methylaminopyrazole 1 g (2.9 mmoles) of 1-benzyl-3-bromo-5-methylamino-4-nitropyrazole are hydrogenated for 8 hours in a solution of 0.29 g (2.9 mmoles) sulfuric acid in 50 ml water according to method (2). After filtering the catalyst and adding 50 ml ethanol, the filtrate is reduced to 30 ml and cooled to –30° C. 244 mg (40 percent of theory) of 4-amino-(3)5-methylaminopyrazole hydrosulfate are obtained in the form of colorless crystals with a melting point of 182° C.

$^1$H-NMR (60 MHz, DMSO-d$_6$):=10.10–9.20 (m; 6H, NH; —NH$_2$; H$_2$SO$_4$; exchangeable with D$_2$O), 7.95 (s; 1H; ring-H) and 2.85 ppm (s; 3H —CH$_3$).

MS (70 eV): m/e=112 (M$^+$).

Production example 28

4-amino-(3)5-ethylaminopyrazole 0.5g (1.31 mmoles) of 1-benzyl-3-bromo-5-ethylamino-4-nitropyrazole are hydrogenated for 8 hours in a solution of 130 mg (1.31 mmoles) sulfuric acid in 50 ml water according to method (2). After filtering the catalyst, the filtrate is reduced to 10 ml. 10 ml ethanol are then added, whereupon the product crystallizes out in the form of colorless crystals with a melting point of 188° C. 0.1 g (34 percent of theory) of 4-amino-(3)5-ethylaminopyrazole hydrosulfate is obtained.

$^1$H-NMR (300 MHz, DMSO-d$_6$):=8.53 (s; wide; 6H, —NH; —NH$_2$; H$_2$SO$_4$; exchanges with D$_2$O), 7.78 (s; 1H; ring-H); 3.21 (q; J=7.1 Hz; 2H; —CH$_2$—CH$_3$) and 1.18 ppm (t; J=7.1 Hz; 3H; —CH$_2$—CH$_3$).

MS (70 eV): m/e=126 (M$^+$).

Production example 29

4-amino-(3)5-(2'-hydroxyethyl)aminopyrazole 1 g (2.9 mmoles) of 1-benzyl-3-bromo-5-(2'-hydroxyethyl)amino-4-nitropyrazole is hydrogenated for 3 hours in a solution of 0.29 g (2.9 mmoles) sulfuric acid in 50 ml water according to method (2). After filtering the catalyst, the solvent is vacuum distilled. The product which crystallizes out is washed with a little ethanol (20 ml) and then dried. 240 mg (35 percent of theory) of 4-amino-(3)5-(2'-hydroxyethyl)aminopyrazole hydrosulfate are obtained in the form of colorless crystals with a melting point of 185° C.

$^1$H-NMR, (60 MHz, DMSO-d$_6$):=8.35 (s; wide; 6H, —NH; —NH$_2$; —OH; H$_2$SO$_4$; exchangeable with D$_2$O), 7.58 (s; 1H; ring-H); 3.55 (m; 2H; —CH$_2$—OH) and 3.15 ppm (m; 2H; —NH—CH$_2$).

MS (70 eV): m/e=142 (M$^+$).

Production example 30

4,(3)5-diaminopyrazole 1 g (2.4 mmoles) of 1-benzyl-5-benzylamino-3-bromo-4-nitropyrazole are hydrogenated in a solution of 0.25 g (2.4 mmoles) sulfuric acid and 50 ml water for 4 hours according to method (2). After filtering the catalyst, 50 ml ethanol are added to the filtrate which is then cooled to –30° C. 184 mg (39 percent of theory) of 4,(3)5-diaminopyrazole hydrosulfate are obtained in the form of colorless crystals with a melting point of 240° C. (decomposition).

Application example:

| | |
|---|---|
| 6.35 g | 4-amino-1-(2'-hydroxyethyl)-5-methylaminopyrazole |
| 2.73 g | 3-aminophenol |
| 10.00 g | lauryl alcohol diglycol ether sulfate sodium salt (28-percent aqueous solution) |
| 10.00 g | ammonia (22-percent aqueous solution) |
| 100.00 g | |

50 g of the hair dye with the composition indicated above are mixed with 50 g hydrogen peroxide solution (6-percent) immediately before using. The mixture is then applied to blond natural hair and allowed to act for 30 minutes at a temperature of 40° C. The hair is then rinsed with water and dried. The hair is dyed a fashionable purple shade.

We claim:

1. A process for making 4,5-diaminopyrazole derivative compounds of the formula (I)

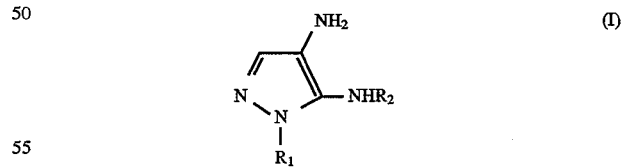

wherein R$_1$ and R$_2$ are independently selected from the group consisting of hydrogen, alkyl radicals having one to six carbon atoms and hydroxyalkyl radicals having two to four carbon atoms, provided that R$_2$ may not be tertiary butyl, said process comprising the steps of:

a) converting 3,5-dibromo-4-nitropyrazole with a member selected from the group consisting of benzyl halide, benzyl sulfate, an alkyl halide radical having one to six carbon atoms, an alkyl sulfate radical having one to six carbon atoms, a hydroxyalkyl halide radical having two to four carbon atoms and a hydroxyalkyl sulfate radical having two to four carbon atoms to form a compound of formula (II):

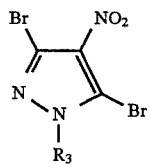
(II)

wherein $R_3$ is selected from the group consisting of alkyl radicals having one to six carbon atoms, hydroxyalkyl radicals having two to four carbon atoms and benzyl radicals;

b) reacting said compound of said formula (II) formed in step a) with a member selected from the group consisting of benzyl amine, alkyl amines having one to six carbon atoms and hydroxyalkyl amines having two to four carbon atoms to form a compound of the formula (III):

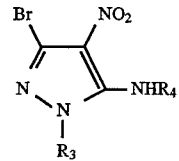
(III)

wherein $R_3$ and $R_4$ are independently selected from the group consisting of alkyl radicals having one to six carbon atoms, hydroxyalkyl radicals having two to four carbon atoms and benzyl radicals; and c) catalytically hydrogenating the compound of formula (III) formed in step b) to obtain a compound of the formula (I).

2. The process as defined in claim 1 wherein said catalytically hydrogenating is performed using a palladium-on-activated-carbon catalyst with a palladium content of 10 percent by weight of said catalyst.

* * * * *